United States Patent [19]
Szycher et al.

[11] Patent Number: 6,117,535
[45] Date of Patent: Sep. 12, 2000

[54] BIOCOMPATIBLE DEVICES

[75] Inventors: Michael Szycher, Lynnfield, Mass.; Alan Edwards, Denbighshire, United Kingdom; Donald Dempsey, Newbury, Mass.; Jacob Leidner, Toronto; David G. Cook, Oakville, both of Canada

[73] Assignee: Cardiotech International, Inc., Woburn, Mass.

[21] Appl. No.: 09/007,220

[22] Filed: Jan. 14, 1998

[51] Int. Cl.[7] ............................................. A61F 2/06
[52] U.S. Cl. ................................... 428/297.7; 428/298.1; 623/1
[58] Field of Search .............................. 428/297.7, 298.1; 623/1

[56] References Cited

U.S. PATENT DOCUMENTS

| | | |
|---|---|---|
| 4,475,972 | 10/1984 | Wong . |
| 4,528,343 | 7/1985 | Kira . |
| 4,738,740 | 4/1988 | Pinchuk et al. . |
| 4,834,746 | 5/1989 | Kira . |
| 4,857,069 | 8/1989 | Kira . |
| 4,871,361 | 10/1989 | Kira . |
| 4,921,495 | 5/1990 | Kira . |
| 4,954,127 | 9/1990 | Kira . |
| 5,064,439 | 11/1991 | Chang et al. ............................. 623/66 |
| 5,132,066 | 7/1992 | Charlesworth et al. . |
| 5,556,426 | 9/1996 | Popadiuk et al. ........................... 623/1 |
| 5,863,627 | 1/1999 | Szycher et al. ......................... 428/36.8 |

OTHER PUBLICATIONS

Hayashi, K. et al., "Elastic properties and strength of a novel small–diameter, compliant polyurethane vascular graft," *J. Biomed. Mater. Res.: Applied Biomaterials* 23(A2)229–244, 1989.

*Primary Examiner*—Elizabeth M. Cole
*Attorney, Agent, or Firm*—Clark & Elbing LLP

[57] ABSTRACT

Filament-reinforced biomedical devices, and methods of making them.

30 Claims, 2 Drawing Sheets

BIOCOMPATIBLE DEVICES

BACKGROUND

The invention relates to polymeric biomedical devices.

The art includes reinforced vascular grafts having single filaments of Dacron or ePTFE.

SUMMARY OF THE INVENTION

The invention features a reinforced biocompatible polymeric device which includes (a) a polymeric base; and (b) a polymeric filament layer on a surface of the base, e.g., wrapped around the polymeric base. The filament layer includes at least three parallel filaments, each independently having a diameter between 100 and 300 microns. The filaments are partially fused or completely fused to the polymeric base and the filaments are at an absolute angle between 70 and 85 degrees to one dimension or axis (e.g., width or, preferably, length) of the device.

In some embodiments, at least three parallel filaments independently have a diameter between 100 and 300 microns; at least three filaments independently have a diameter between 150 and 250 microns; the polymeric filament layer includes parallel filaments having the same diameter (within 5% or 10%); or the filament layer is a first filament layer, and the device further includes a second polymeric filament layer; or combinations thereof. The second polymeric filament layer, if present, includes at least two parallel filaments, each independently having a diameter between 100 and 300 microns. In other embodiments, the device includes between 2 and 10 filament layers, or between 5 and 8 filament layers. The filament layer adjacent to the polymeric base can be partially fused to the base, and can be removed during use without damaging the structural integrity of the polymeric base. A filament can contain a polymer selected from polyurethane (e.g., Chronoflex AL 65D), polycarbonate, nylon, acrylic, and polysulfone.

The polymer base of the device can include, for example, a biodurable polycarbonate polyurethane block copolymer. This block copolymer includes: (a) a polycarbonate glycol internal segment; (b) a polyurethane internal segment; (c) a polydialkylsiloxane internal segment; (d) di($C_{1-6}$ alkyl) amino or $C_{1-6}$ hydroxyalkyl terminating segments; (e) cyclo ($C_{5-7}$ alkane)diamino or cyclo($C_{5-7}$ alkane)dihydroxy internal segments; and (f) $C_{2-8}$ alkylene diamino or dihydroxy internal segments The segments are linked by linkages selected from urethane, urea, and C—Si—C moieties, and the block copolymer is preferably devoid of hydrolytically unstable Si—O—C linkages and is also substantially devoid of ether linkages. In other embodiments, at least 30% by weight (e.g., at least 40%, at least 50%, or at least 70% by weight) of the polymer base is the biodulrable polycarbonate polyurethane block copolymer.

According to one aspect, the device is a vascular graft. The graft includes a graft wall base (polymeric base), and a filament layer wrapped around the outer surface of the graft wall base. The polymeric base is a graft wall that is an anisotropically microporouls single layer with a porosity between 60% and 80% void/volume (e.g., between 65% and 75% void!volume). The -raft can have a compliance between 2% and 10%, or between 4% and 7%. In some embodiments, (a) the graft wall has a filament layer and has a compliance that is between 0.5% and 2.5% less than the compliance of the graft wall without a filament layer; (b) the graft has an internal diameter between 2.8 mm and 6.2 mm, e.g., between 4.8 and 6.2 mm; (c) the graft has a wall thickness between 0.2 and 1.05 mm, e.g., between 0.8 and 1.05 mm, (d) the graft has a radius of kinking between 5 mm and 12 mm and a wall thickness between 0.6 mm and 0.8 mm; (e) the graft has a second filament layer which includes two parallel filaments; (f) the second filament layer includes three parallel filaments; (g) the graft includes a plurality of parallel filament layers, e.g., a plurality between 1 and 8 layers, or between 2 and 3 layers; (h) the absolute angle between the filaments of a filament layer and the length of the graft is between 70 and 85 degrees, e.g., between 75 and 85 degrees, or between 78 and 82 degrees; or combinations thereof.

The invention also includes a method of making a reinforced vascular graft. This method includes: wetting a plurality of polymeric filaments with a solvent; wrapping the wetted plurality of filaments around the -raft at an absolute angle between 70 and 85 degrees to the length of the graft, wherein the filaments in the plurality are parallel to each other; and allowing the solvent to evaporate. In some embodiments, the plurality of filaments is between 3 and 6, and is preferably 3. The method can further include repeating the wrapping step in the reverse or opposite direction (before or after the solvent evaporates) with at least one, and preferably 2 or 3 filaments. One embodiment includes 2 layers; a first layer wrapped at between 78 and 85 degrees in one direction and a second layer wrapped at between 78 and 85 degrees in the other direction (e.g. +85 degrees and −85 degrees relative to the linear axis, respectively).

DETAILED DESCRIPTION OF THE INVENTION

Figure 1:
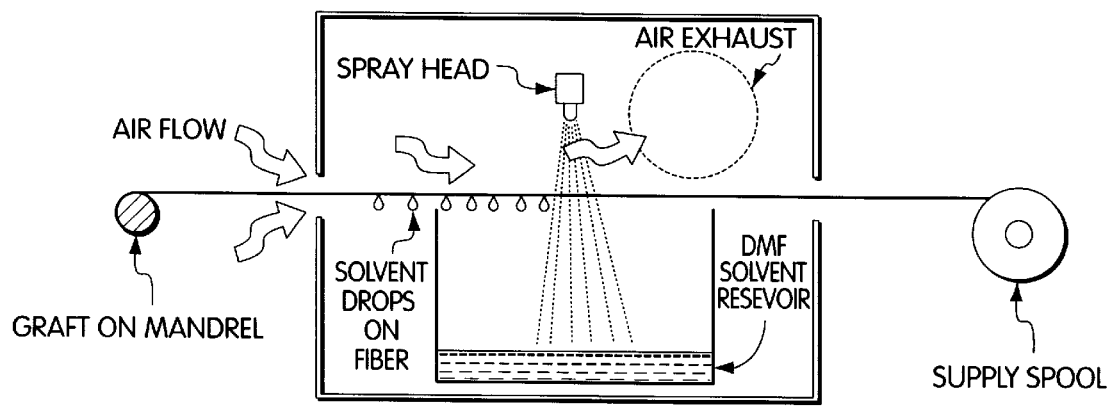
FIG. 1 is a schematic of a solvent spraying chamber used to treat a filament before rapping the filament onto a biocompatible device.
Figure 2:
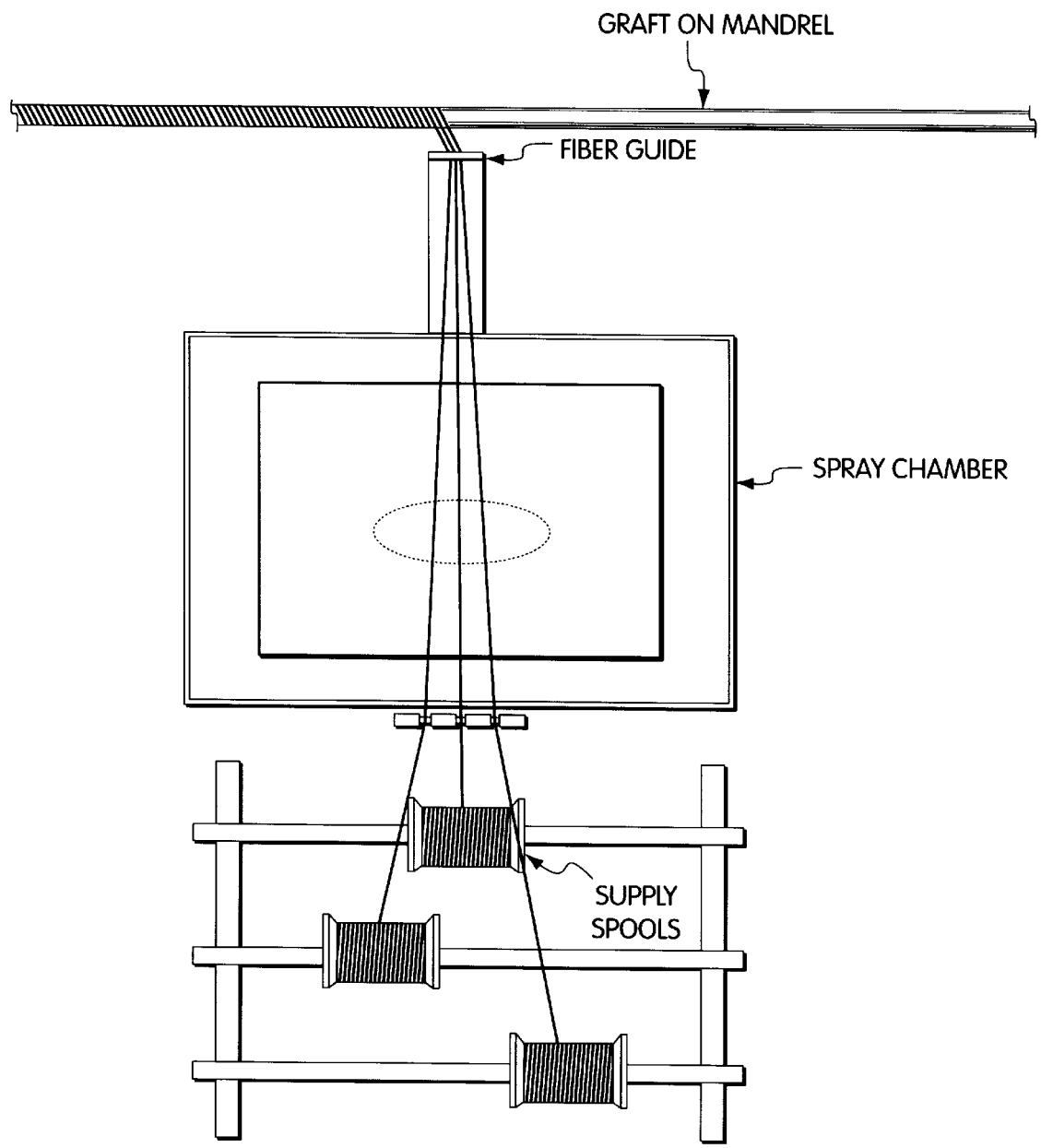
FIG. 2 is a bare schematic of an apparatus adapted to wrap three parallel filaments onto a vascular graft.

The invention also features polymeric biocompatible devices reinforced with one or more layers of parallel polymeric filaments having a diameter between 100 and 300 microns, e.g., about 200 microns. The filaments are wrapped around a polymeric base.

A biocompatible device is a device intended to contact cells, biological fluids, and preparations derived from cells. Cells include individual cells; animal tissues such as blood, muscle, nerves, tendons, cartilage, bone, and vasculature including veins, arteries, valves, and placental material and organs of animals; and tissues of plants. Biological fluids include blood, urine, tears, cytoplasm, spinal fluid, amniotic fluid, semen, bile, and saliva. Preparations derived from cells include homogenized cell or receptor preparations, cryogenically prepared tissue slices, centrifugally-isolated fractions, and ex vivo cell cultures. In general, a biocompatible device is chemically inert (e.g., nontoxic) to normal cells, fluids, and cell-derived preparations, although in some cases, the device may be designed to release, leach, or selectively bind biologically active substances. A biocompatible device includes a base and a filament layer. Filament reinforcement improves graft kink resistance.

A polymeric base is a portion of the device, which portion contacts a polymeric filament. A polymeric base can include polymers such as polyurethanes, e.g., polycarbonate polyurethanes. The segments of this polymer are linked by urethane, urea, and C—Si—C moieties. This block copolymer is devoid of hydrolytically unstable Si—O—C linkages and being substantially devoid of ether linkages.

Upon contact with an appropriate solvent, a polymeric base (or a alternatively, a filament) becomes slightly tacky, sticky, softened, or solubilized, to allow a polymeric filament to fuse to the polymeric base. The degree of fusion may be partial or complete. In some embodiments, a filament is partially fused and can be manually removed to expose the polymeric base, for example, by a surgeon before implantation of the device, without substantial damage to the polymeric base. Where complete fusion occurs, removal of a filament is difficult or possibly destructive. The extent of fusion between the base and a filament is controlled by factors such as the base polymer, the filament polymer, the type and amount of solvent, and the pressure or tension with which the filament is wrapped. In some embodiments, the polymeric base polymer is at least 50%, 75%, 85%, or 90% by weight of the composition of the device.

A polymeric filament has a diameter between 100 and 300 microns. Preferably the filament diameter is between 150 and 250 microns, e.g., between 180 and 240 microns, plus or minus a standard deviation between about 10 and 35 microns. For example, one preferred range is between 115 and 285 microns. According to the present invention, small diameter filaments are preferable to large diameter filaments; for example, they present a smaller obstruction to needle penetration, thereby improving access. Filaments within a layer (parallel filaments) or filaments from different layers can be of the same or different diameter. A polymeric filament can include polymers such as polypropylene, PTFE, and preferably polyurethanes, nylon, polysulfone, and acrylic. Examples include Chronoflex AL65D (CardioTech International, Woburn, Mass.), Dacron, or PTFE. In general, a filament should have a Shore hardness of between 55D and 75D, for example, between 60D and 70D, or about 65D. A plurality of filaments are applied in parallel to achieve optimal kink resistance, "feel", and flexibility. A plurality of filaments is at least two, e.g., at least 3, at least 4, at least 5, or between 2 and 20, or between 2 and 7. In one embodiment, two or at most three passes are preferred. Parallel filaments do not cross each other, and are preferably applied simultaneously. Additional solvent or adhesive may be used to attach a filament to either the polymer base or another filament layer. The filaments are wrapped around the device at an absolute angle between 70 and 85 or between 75 and 85 degrees to the length of the device (e.g. between −75 and −85 degrees or between +75 and +85 degrees). For example, if the device is a graft, the angle can be measured along the length of the graft or, equivalently, the length of the mandrel holding the graft. In some embodiments, the absolute angle is between 78 and 82 degrees. A plurality of filaments provides even coverage around the selected portion of the polymer base with fewer layers while maintaining flexibility and kink resistance. In contrast, wrapping multiple layers of a single filament, in other words, multiple passes back and forth across a device, generally produces a significantly less even coverage around the polymer base. Less even coverage includes filaments from different layers tending to bunch or slide together. In addition, too many layers results in undesirably stiff graft with poor compliance.

Filaments may be applied in one or, preferably, a plurality of layers. A plurality of layers is at least 2, at least 3, or between 2 and 15, or between 2 and 10, or between 5 and 8, e.g., 6. A first filament layer is adjacent to the polymeric base, namely, it is applied directly to the polymeric base, e.g., a vascular graft or valve. A second filament layer, if any, is applied over the first filament layer with an offset, advance, or overlap to position filaments of the second layer between or, alternatively, across, the filament spirals of the first layer to more evenly distribute the filaments. The second filament layer may or may not contact the polymeric base directly. The filaments should not be wrapped so tightly as to interfere with the performance of the device, e.g., the compliance of a graft.

The biocompatible device can be a vascular graft. Vascular grafts are preferably biodurable, non-thrombogenic, chemically durable, resistant to infection or formation of microbial plaques, technically easy to implant, and have the elastic properties of the saphenous vein. In the case of vascular grafts, the polymeric base is the graft wall base, preferably an anisotropically microporous single layer with a porosity between 60% and 80% (void to volume). A graft has a compliance or dynamic compression between 2% and 10%, preferably between 3% and 7%. For example, using a systolic pressure of 120 mm Hg and a diastolic pressure of 80 mm Hg, representing $\Delta$40 mm Hg, a change of 4 mm Hg would be 10% compliance (4/40), or about 0.1% /mm Hg. The internal diameter of a graft is between 2.8 mm and 6.2 mm, e.g., between 4.8 and 6.2 mm. The wall thickness of a graft is between 0.2 and 1.0 mm, e.g., between 0.8 and 1.0 mm. Preferably, the radius of kinking is between 5 and 12 mm after the filament layer or layers are applied to a graft having a thickness between 0.8 and 1.0 mm. The vascular grafts of the invention include small diameter microporous vascular grafts which are self-sealing, non-thrombogenic, puncture resistant, kink-resistant, compliant, and which provide superior pulsatile in situ. (see Examples 3–10 below). Performance can be further enhanced by bonding platelet inhibiting drugs onto the inner surface of the graft, improving the surface for endothelial cell attachment, and tapering one or both ends of the graft. The preferred grafts of the invention have internal diameters which expand to accommodate a pulsatile flow without significant expansion of the external diameter.

A preferred embodiment features a polymeric base (e.g., a vascular graft wall) comprising a biodurable block copolymer. This block copolymer includes: (a) a polycarbonate glycol internal segment; (b) a polyurethane internal segment; (c) a polydialkylsiloxane internal segment; (d) di($C_{1-6}$ alkyl)amino or $C_{1-6}$ hydroxyalkyl terminating segments; (e) cyclo($C_{5-7}$ alkane)diamino internal segments; and (f) C2-4 alkylene diamino internal segments. The segments are linked by urethane, urea, and C—Si—C moieties. With attention to the terminating segments and the formation of the polysiloxane, the polysiloxane, and in turn, the block copolymer, are devoid of hydrolytically unstable Si—O—C linkages. With attention to the temperature and other conditions with which the polycarbonate is manufactured, the polycarbonate, and in turn, the block copolymer, are substantially devoid of ether linkages. "Substantially devoid of ether linkages" means no ether linkages are detected by FTIR analysis.

The disclosed block copolymer can be obtained, for example, by reacting reactants including: (a) an aromatic or aliphatic diisocyanate; (b) a polycarbonate diol; (c) a difunctional polydialkylsiloxane (e.g., polydi(fluoroalkyl) siloxane) having a viscosity between 15 and 70 centistokes; (d) two chain extenders independently selected from $C_{2-8}$ diamines and $C_{2-8}$ diols; and (e) a $C_{2-6}$ alkanol or di($C_{2-6}$ alkyl) amine chain terminator, or mixture thereof. Regarding the chain extenders, the diamines and diols are cyclic, straight chain, or branched, and at least one chain extender is cyclic or branched. The copolymer is devoid of hydrolytically unstable Si—O—C linkages and substantially devoid of ether linkages.

One preferred block copolymer is obtained by reacting (a) 4,4-diphenyl methane diisocyanate or methylene bis (4-cyclohexyl isocyanate); (b) a polycarbonate diol having a molecular weight between 1000 and 3000 Daltons; (c) a polydimethylsiloxane having a viscosity between 15 and 70 centistokes (e.g., 50–60 centistokes); (d) ethylene diamine and a cyclohexane diamine (e.g., 1,3-cyclohexane diamine); and (e) a dialkylamine having between 2 and 6 carbon atoms (e.g., diethylamine).

Having described some of the advantages of the disclosed block copolymers, some methods for making them are described below. One method includes forming a prepolymer by combining a diisocyanate with a difunctional polydialkyl siloxane and a polycarbonate diol in a polar solvent such as cyclohexanone, N-methyl pyrrolidone, dimethyl acetamide, or dimethyl formamide. A mixture of at least two chain extenders and at least one chain terminator is prepared in a polar solvent. The chain extenders are independently selected from $C_{2-8}$ diamines and $C_{2-8}$ diols, wherein the diamines and diols are cyclic, straight chain, or branched. In one embodiment, at least one chain extender is cyclic or branched. The chain terminator is a $C_{2-6}$ alkanol or di($C_{2-6}$ alkyl) amine. After step (a), the prepolymer is chain extended by adding the mixture of chain extenders and chain terminator(s) with agitation, to produce the block copolymer. The difunctional polydialkylsiloxane may be replaced with a difunctional polydi(fluoroalkyl)siloxane, or a mixture of both alkyl and fluoroalkyl siloxanes.

Diisocyanates are aromatic or aliphatic diisocyanates such phenyl diisocyanate, toluene diisocyanate, isophorone diisocyanate, p-trimethylxylylene diisocyanate, m-trimethylxylene diisocyanate, and preferably 4,4-diphenyl methane diisocyanate or methylene bis (4-cyclohexyl isocyanate).

Difunctional siloxanes may be dialkylsiloxanes, wherein each alkyl group is independently selected from $C_{1-4}$ alkyl, each alkyl being optionally and independently substituted with one or more halogen atoms, such as chlorine, bromine, iodine, and preferably fluorine. Thus, dialkylsiloxanes include poly(dimethyl)siloxane, poly (methylethyl)siloxane, di($C_{1-3}$ fluoroalkyl)siloxanes, and poly ($C_{1-3}$ alkyl $C_{1-4}$ fluoroalkyl)siloxanes. Examples include polydi (perfluoromethyl)siloxane, poly(methyl 3,3,3-trifluoropropyl)siloxane, and poly (methyl perfluoroethyl) siloxane. Examples of fluoroalkyls include fluoromethyl, difluoromethyl, trifluoromethyl or perfluoromethyl, 2-perfluoroethyl, 3,3-difluoropropyl, and 3-perfluoropropyl (or 3,3,3-trifluoropropyl). In some embodiments, to increase the effect of the halogen atoms without adding too much weight, each halogen atom is on the terminal methyl group (s) of the alkyl substituents bonded to the Si atom. A difunctional siloxane reagent has terminating groups selected from $C_{1-6}$ aminoalkyl and $C_{1-6}$ hydroxyalkyl. The terminating groups preferably have between 2 and 4 carbon atoms, such as aminopropyl and hydroxypropyl. The molecular weight of a siloxane is between 800 and 30,000 Daltons, and preferably between 1000 and 3000 Daltons. Commercially available siloxanes have viscosities between 10 and 2000 centistokes, and preferably between 15 and 75 centistokes (e.g., between 20 and 60 centistokes). For example, available siloxanes have viscosities of 10–15, 20–30, 50–60, 100–120, and 2000 centistokes. Lower viscosities generally produce stiffer copolymers which are less suitable for vascular grafts.

Polycarbonates are polyethylene polycarbonates having a molecular weight between 500 and 5000 Daltons, and preferably between 1000 and 3000 Daltons.

Chain extenders are short chain diamines or diols having between 2 and 7 carbon atoms, such as isobutane, cyclopentane, cyclohexane, and cycloheptane. Examples include ethylene glycol, 1,3-propylene glycol, 1,4-butane diol, 1,5-pentane diol, 1,6-hexane diol, 1,4-cyclohexane diol, 1,4-isophorone diol, and the corresponding diamines. Preferred chain extenders include 1,3-cyclohexane diamine, ethylene diamine, and the corresponding diols. The molar ratio of at least one branched or cyclic chain extender to isocyanate groups is generally between 3.1:100 and 5.5:100, and preferably is about 3.8:100. The molar ratio of a second chain extender to isocyanate groups is between 29:100 and 48:100, and preferably is about 35:100.

Chain terminators are monofunctional dialkylamines or alkanols having between 2 and 4 carbon atoms, such as diethylamine or hydroxypropyl. The molar ratio of the chain terminator to isocyanate groups is between 0.1:100 and 2.0:100, and is preferably about 1.5:100.

One embodiment of the invention features a polycarbonate polyurethane block copolymer obtained by reacting (a) 4,4-diphenyl methane diisocyanate or methylene bis (4-cyclohexyl isocyanate); (b) a polycarbonate diol having a molecular weight between 1000 and 3000 Daltons; (c) a polydimethylsiloxane terminated with aminopropyl groups, and having a molecular weight between 1000 and 3000 Daltons; (d) a $C_{2-4}$ alkylene diamine and a cyclohexanediamine; and (e) diethylamine. For example, the molar proportions of one preferred quadripolymer (consisting of (a) 4,4-diphenyl methane diisocyanate; (b) polycarbonate diol having a molecular weight between 1000 and 3000 Daltons; (c) ethylene diamine and 1,3-cyclohexanediamine; (d) a polydimethylsiloxane devoid of Si—O—C bonds, terminated with aminopropyl groups, and having a molecular weight between 1000 and 3000 Daltons; and (e) diethylamine) are, respectively, about (a) 100, (b) 59.5 1, (c) 35 and 3.9, (d) 0.8, and (e) 1.47; or within 10% or 5% thereof.

Hydroxypropyl terminated siloxanes are prepared by reacting difunctional silicon hydrides with allyl alcohol in the presence of a precious metal catalyst. It is important to recognize this hydroxyl functional polymer is devoid of unstable Si—O—C bonds, and therefore the resultant polyurethane will also be devoid of Si—O—C bonds. The molecular weight of the polyglycol can vary from 800 to 30,000 Daltons, and preferably is between 1500 and 3000. Similarly, the invention features the use of materials such as isocyanate terminated silicone oligomers synthesized using the reaction of difunctional silicon hydrides with allyl isocyanate in the presence of a precious metal catalyst, such as platinum, in catalytic amounts (e.g., 1–50 ppm, such as 5 or 10 ppm). The molecular weight of the polyisocyanate can vary from 800 to 30,000 Daltons, and preferably is between 1500 and 3000.

Other cardiovascular devices are related to (a) angiography and angioplasty (diagnostic and therapeutic catheters such as small-diameter grafts, intra-operative balloon catheters, laser catheters, guiding catheters, stents, and atherectomy devices), (b) arrhythmia control (coatings and housings of electronic devices), (c) cardiovascular surgery (implantable devices or surgical equipment, such as mechanical and tissue valves, ventricular assist devices, pace maker parts, automatic implantable cardioverter, and defibrillators), and (d) cardiac assist devices.

Vascular grafts

A vascular graft can be made according to U.S. Pat. No. 5,132,066 (Charlesworth et al.). Briefly, a polymer composition, as described above, is combined with porosifiers or fillers, a surfactant system, and a solvent. The polymer solution is extruded into a coagulant. After coagulation, the -raft is removed from the mandrel. After coagulation, further treatments may be suitable for certain applications. The single layer structure avoids delamination, maintains cross section, and allows even and clean cutting of the device, e.g., the craft. An open pore structure in the mid-portion of the wall allows wall compression relating to pulsatile flow. The physical characteristics of the graft wall, including thickness, porosity, permeability, and compliance, are determined by the mandrel rotation and transverse speed, extrusion head rotation speed, and polymer pump pressure.

The physical characteristics of devices made from the disclosed copolymers are discussed next.

Physical Characteristics

International quality control standards include the Draft European Standard and the revised A.A.M.I. Standard. Safety testing includes procedures described in CEN/TC 28/WG 3/TF2: "Vascular Prostheses and Cardiovascular Patches. PrENxx203-02 Particular Requirements". Test methods for physical characteristics are known to those in the art, and are described, for example, in the ISO/DIS 7198 (ISO/TC 150/SC 2 N169). These physical characteristics include porosity, suture retention strength, kink diameter/radius, compliance, porosity, water permeability, integral water leakage, water entry pressure, circumferential tensile strength, longitudinal tensile strength, burst strength, diaphragm burst strength, probe burst strength, pressurized burst strength, strength after repeated puncture, usable length, relaxed internal diameter, pressurized internal diameter, and wall thickness. Some physical characteristics are highlighted below.

First, compliance is the ability of a prosthesis to elastically expand and contract in the circumferential direction in response to a pulsatile pressure. Compliance is important for matching prostheses to the arterial tree, and may be important to the clinical performance of small diameter grafts in low flow situations such as below knee arterial bypasses. When a graft relies on overall external dilation, perivascular ingrowth prevents long-term compliance. However, the disclosed grafts rely on wall compression, i.e., provide internal dilation or lumenal expansion without significant external dilation by compressing the graft wall. It then follows that the disclosed grafts are less susceptible to perivascular ingrowth and have longer-term compliance and improved transmission of energy. Compliance can be measured based on longitudinal stretch inflation tests, and uniaxial rigidity tests according to methods known to those in the art, such as Stewart S. F. C. and Lyman, D. J., J. Biomechanics 23:629–637 (1990).

Second, leakage is the volume of clean, filtered liquid with a viscosity approximating that of water) which passes through flaws in a water-impermeable vascular prosthesis in a specified time under a specified pressure. Leakage may be through small defects in the wall of through an anastomosis constructed by the manufacturer. The vascular grafts made from the disclosed block copolymers control permeability and blood leakage through the wall of the graft by manipulating pore size in the inner and outer skins. The disclosed grafts do not require, for example, the use of gelatin to reduce blood leakage.

Third, porosity is the estimate or index of the ratio of the void within a material to the total volume occupied by the material including the voids, expressed as the percentage void to the total area of volume, mean distance between nodes, or mean pore diameter. Porosity can be measured by planimetric, gravimetric, or microscopic methods. The disclosed grafts are made of a microporous copolymer, in contrast to a graft made of solid filaments woven or wrapped in layers, with interstices between the filaments and between the layers of filaments.

Other features and advantages of the invention are apparent from the examples below.

EXAMPLES

Example 1

Preparation of fiber

Chronoflex AL-65D was dried in a desiccating dryer at 50° C. for several days or 54° C. for 24 hours. Dryness of the resin was confirmed by dewpoint measurement of the dryer outlet air. The dried resin was extruded with a 0.75 inch diameter single screw extruder with a 1.73 mm orifice die. The extruder operating temperatures for zones 1, 2, 3, and the die were 190, 210, 210, and 212° C. respectively. The extruded fiber was drawn down and collected onto a 4 inch diameter take-up spool with servo controlled motor speed. Filament batches were prepared and measured for average diameter as shown in Table 1.

TABLE 1

Prepared Polyurethane Microfibers

| Run # | Extruder RPM | Spool RPM | Average Fiber Diameter ($\mu$m) | Standard Deviation ($\mu$m) |
|---|---|---|---|---|
| 1 | 4.1 | 160 | 248 | 34 |
| 2 | 2.5 | 120 | 209 | 18 |
| 3 | 4.0 | 150 | 205 | 30 |
| 4 | 2.9 | 135 | 200 | 17 |
| 5 | 3.2 | 135 | 194 | 20 |

As freshly solidified polyurethane remains tacky for several minutes, the freshly spun filament was allowed to sit on the take-up spool for at least 30 minutes before being transferred to another reel for storage. These were subsequently rewound onto smaller supply spools for the wrapping apparatus described below.

Graft Wrapping

The method for making filament wrapped graft includes (a) wetting a polyurethane fiber with DMF solvent, (b) wrapping the solvent-softened fiber around a rotating graft, and (c) evaporating the solvent from the fiber.

The solvent spray chamber is shown in FIG. 1. The amount of solvent deposited on the fiber must be sufficient for adhesion of a filament to a graft and yet not so much that the fiber line breaks or clumps. Also, the solvent must be evaporated at a rate fast enough to avoid clumping of filaments or excessive wetting of the graft, and yet slow enough to allow adhesion of the fiber to the graft. Due to negative pressure of the exhaust suction applied to the spraying chamber, droplets of solvent adhering to the sprayed filament are knocked off as the filament exits the chamber. In some embodiments, freshly made filaments are preferred because older filaments absorb DMF more slowly than freshly spun filaments. The solvent can be recycled after spraying by collecting and reusing the overspray. Due to water absorption by DMF, the preferred solvent, the solvent is recycled for about one hour before being discarded.

The tension applied to the filament during wrapping must be sufficient to adhere to the graft, and yet not high enough to break the line or cause constriction of the inner diameter of the graft. For a diameter of about 200 microns, the tension should be between 15 and 20 grams.

In one aspect, the invention features wrapping a filament with a diameter of about 200 microns at a graft angle of about 85° six to ten times around a graft having an external diameter of 5 or 6 mm and an internal diameter of about 4 mm. The filaments may be arranged to have multiple wraps in one pass on the graft to ensure evenly spaced filaments as shown in Figure II. The filament guide head hole spacing can be calculated by determining the advance of the mandrel as π D cos (theta) where theta is the fiber to graft angle and D is the outer graft diameter. This value is divided by 4 to give the proper hole spacing. For example, with fiber angle, theta=85° and D=6 mm, then advance=1.638 mm. Therefore, the hole spacing=1.638/4=0.4095 mm.

Single wrapped or three fiber wrapped grafts were made using the conditions in Table II with the filaments in Table III.

TABLE II

| | |
|---|---|
| Mandrel RPM | .90 |
| Mandrel Transverse motor RPM | 117 |
| Graft angle | 85° |
| N₂ spray pressure | .20 PSIG |
| Spray head valve opening | ½ turn open |
| (~675 mL DMF solvent/hour) | |
| Filament drag force (15 grams line tension) | 43 grams |
| Distance between filament and spray head | .3 cm |
| Distance between sprayer and solvent (siphon head) | ~12 cm (4.75") |
| Distance between filament guide and graft | 2–5 mm |
| Air flow at spray chamber exit slot | ~2000 ft/min. |

TABLE IIIa 0.20 mm diameter filament, single filament pass

| graft used | # of layers |
|---|---|
| 96-J22-P0221 | 6 |
| 97-J22-P076 | 10 |

TABLE IIIb 0.20 mm diameter filament, three filament pass

| graft used | # of layers |
|---|---|
| 97-J22-P081 | 2 × 3 = 6 |
| 97-J22-P081 | 3 × 3 = 9 |
| 97-J22-P079 | 3 × 4 = 12 |

TABLE IIIc 0.25 mm diameter filament, three filament pass

| graft used | # of layers |
|---|---|
| 97-J22-P078 | 2 × 3 + 1 = 7 |
| 97-J22-P077 | 2 × 3 = 6 |
| 97-J22-P077 | 3 + 2* = 5 |
| 97-J22-P079 | 2 × 3 = 6 |
| 97-J22-P080 | 3 × 3 = 9 | one filament broke on second pass

TABLE IV

| | |
|---|---|
| Mandrel diameter | 5.9 mm |
| Mandrel RPM | 90 |
| Mandrel transverse motor RPM | 135 |
| Resulting graft angle | 85° |
| Number of passes (layers) | 2 × 3 |
| N₂ spray pressure | 20 PSIG |

TABLE IV-continued

| | |
|---|---|
| Spray head valve opening | ¾ turn open |
| (~725 mL DMF solvent/hour) | |
| Filament drag force | 48 grams |
| (= 20 grams line tension) | |
| Distance between filament and spray head | 3 cm |
| Distance between sprayer and solvent (siphon head) | ~12 cm |
| Distance between filament guide and graft | .2–3 mm |
| Air flow at spray chamber exit slot | ~2000 ft/min. |

TABLE V

| | |
|---|---|
| Mandrel diameter | 4.8 mm |
| Mandrel RPM | 90 |
| Mandrel transverse motor RPM | 117 |
| Graft angle | 85° |
| Number of passes (layers) | 2 × 3 |
| N₂ spray pressure | 20 PSIG |
| Spray head valve opening | ¾ turn open |
| (~725 mL DMF solvent/hour) | |
| Filament drag force | 48 grams |
| (= 20 grams line tension) | |
| Distance between filament and spray head | 3 cm |
| Distance between sprayer and solvent (siphon head) | ~12 cm |
| Distance between filament guide and graft | 2–3 mm |
| Air flow at spray chamber exit slot | ~2000 ft/min. |

Example 2
Vascular Access and Biodurability In Vivo

Two 5 mm ID grafts are implanted as carotoid artery interposition grafts in each of four dogs. The implants are explanted after six, fifteen, and twenty-two weeks and examined for cracks or other undesirable events. Light microscopy between 40× and 1100 ×, e.g., up to 400×, 800×, or 1000×, can be used to show the extent of neointima lining the anastomotic region of the graft, the extent of lumenal reduction, and the composition of the surrounding capsule.

Example 3
Vascular Access and Biodurability In Vivo

Two 5 mm ID grafts are implanted as bilateral aorta-femoral bypasses with the iliac arteries tied off. Over a period between 6 and 24 months, patency is monitored by color-coded Duplex examination, Doeppler analysis, or angiography.

Example 4
Kink Resistance

Following ISO/TC 150/SC 2 N169 or ISO/DIS 7198, radius templates or cylindrical mandrels ranging from 4 to 50 mm in diameter are used. Water-permeable constructions are tested at ambient pressure. Samples are placed in a radius template that does not cause kinking or narrowing. The radius template is decreased until slight narrowing or kinking occurs. The radius of the mandrel that first causes kinking is recorded. Alternatively, a loop of the sample is formed and the ends are pulled in opposite directions until a kink is observed. An appropriate size cylindrical mandrel is placed within the loop to measure the kink radius. A radius of kinking between 5 and 12 mm is generally desirable for vascular grafts.

Example 5
Dynamic Compliance

Dynatek Laboratories provides a calibrated positive displacement instrument that measures dynamic compliance over a pressure excursion of 80 mm Hg to 120 mm Hg at a cycle rate of seventy-two beats per minute. Grafts having a compliance between 2% to 10% and preferably 3% to 7% radial compliance were been prepared.

Example 6
Pulsatile Flow In Situ

Pulsatile flow is measured using digital subtraction angiography as described by Seifalian, A. M. *Vascular Imaging for Surgeons*, R. M. Greenhalgh, ed., W. B. Saunders ISBN 0-7020–2015-X 1995.

Example 7
Self-Sealing

An artificial circuit working at a 120 nm Hg, circulating water at 37° C. is used. The graft are punctured with a 16 gauge dialysis needle and the needle is withdrawn. The punctured site is photographed immediately after needle withdrawal. If practicable, water loss is measured.

Example 8
Strength after Repeated Puncture

According to ISO/DIS 7198, 8.3.4, repeated punctures per square centimeter (0, 8, 16, and 24) simulate months of dialysis use (respectively, 0, 6, 12, and 18). At least three samples are treated for each test condition. The respective mean radial tensile strengths (N/nm) are calculated and compared with the strength of similarly-treated, commercially available materials such as expanded PTFE, or materials which are filament-wrapped or are without a filament wrap. After 18 months, the reduction in radial tensile strength was about 15%.

Other Embodiments

Based on the description and examples herein, a person of skill would be able to understand the essential features of the invention and without departing from the spirit and scope thereof, adapt the invention to various conditions and usages.

What is claimed is:

1. A reinforced biocompatible polymeric device, comprising
   (a) a polymeric base; and
   (b) a polymeric filament layer wrapped around said polymeric base, said filament layer comprising at least three parallel filaments each independently having a diameter between 100 and 300 microns, wherein said filaments are partially fused or completely fused to said polymeric base and said filaments are at an absolute angle between 70 and 85 degrees to the length of the device.

2. A device of claim 1 wherein said filament layer consists of three parallel filaments.

3. A device of claim 1 wherein said filaments independently have a diameter between 150 and 250 microns.

4. A device of claim 1 having a polymeric filament layer comprising parallel filaments having the same diameter.

5. A device of claim 1 wherein said filament layer is a first filament layer, further comprising a second polymeric filament layer comprising at least two filaments parallel to each other, each independently having a diameter between 100 and 300 microns.

6. A device of claim 2, further comprising between 1 and 9 additional filament layers.

7. A device of claim 6 comprising between 4 and 7 additional filament layers.

8. A device of claim 1 wherein the filament layer adjacent to said polymeric base is removably fused to said base.

9. A device of claim 1 comprising a filament containing a polymer selected from polyurethane, polycarbonate, nylon, acrylic, and polysulfone.

10. A device of claim 1 wherein said polymer base comprises a biodurable polycarbonate polyurethane block copolymer comprising
    (a) a polycarbonate glycol internal segment;
    (b) a polyurethane internal segment;
    (c) a polydialkylsiloxane internal segment;
    (d) di($C_{1-6}$ alkyl)amino or $C_{1-6}$ hydroxyalkyl terminating segments;
    (e) cyclo($C_{5-7}$ alkane)diamino or cyclo($C_{5-7}$ alkane) dihydroxy internal segments; and
    (f) $C_{2-8}$ alkylene diamino or dihydroxy internal segments; wherein said segments are linked by urethane, urea, and C—Si—C moieties, said block copolymer being devoid of hydrolytically unstable Si—O—C linkages and being substantially devoid of ether linkages.

11. A device of claim 10 wherein said polycarbonate polyurethane comprises the product of reacting
    (a) 4,4-diphenyl methane diisocyanate or methylene bis (4-cyclohexyl isocyanate);
    (b) a polycarbonate diol having a molecular weight between 1000 and 3000 Daltons;
    (c) a polydimethylsiloxane having a viscosity between 50 and 60 centistokes;
    (d) ethylene diamine
    (e) a cyclohexane diamine; and
    (f) a dialkylamine having between 2 and 6 carbon atoms.

12. A device of claim 10 wherein at least 30% by weight of said polymer base is said biodurable polycarbonate polyurethane block copolymer.

13. A device of claim 12, wherein at least 50% by weight of said polymer base is said block copolymer.

14. A device of claim 10 wherein said device is a vascular graft comprising a graft wall base, and a filament layer wrapped around the outer surface of said graft wall base.

15. A graft of claim 14, wherein said polymeric base is a graft wall that is an anisotropically microporous single layer with a porosity between 60% and 80% void/volume.

16. A graft of claim 15 having a compliance between 2% and 10%.

17. A graft of claim 16 having a compliance between 4% and 7%.

18. A graft of claim 15, wherein said graft wall has a filament layer and has a compliance that is between 0.5% and 2.5% less than the compliance of the graft wall without a filament layer.

19. A graft of claim 15 having a vascular shape with an internal diameter between 4.8 and 6.2 mm.

20. A graft of claim 19 having an internal diameter between 4.8 and 6.2 mm.

21. A graft of claim 15 having a wall thickness between 0.2 and 1.05 mm.

22. A graft of claim 21 having a wall thickness between 0.8 and 1.05 mm.

23. A graft of claim 15 having a radius of kinking between 5 mm and 12 mm and a wall thickness between 0.6 mm and 0.8 mm.

24. A graft of claim 15, wherein said filament layer comprises two parallel filaments.

25. A graft of claim 15, wherein said filament layer comprises three parallel filaments.

26. A graft of claim 15, further comprising a plurality of parallel filament layers.

27. A graft of claim 17 wherein said plurality is between 1 and 8 layers.

28. A graft of claim 27 wherein said plurality is between 2 and 3 layers.

29. A graft of claim 15 wherein the absolute angle between the filaments of a filament layer and the length ot the graft is between 75 and 85 degrees.

30. A graft of claim 29 wherein said angle is between 78 and 82 degrees.

* * * * *

UNITED STATES PATENT AND TRADEMARK OFFICE
CERTIFICATE OF CORRECTION

PATENT NO. : 6,117,535  
DATED : September 12, 2000  
INVENTOR(S) : Michael Szycher, Alan Edwards, Donald Dempsey, Jacob Leidner, and David G. Cook Page 1 of 1

It is certified that error appears in the above-identified patent and that said Letters Patent is hereby corrected as shown below:

Column 1,  
Line 58, "microporouls" should be -- microporous --.  
Line 60, "void! volume" should be -- void/volume -- and "-raft" should be -- graft --.

Column 2,  
Line 15, "-raft" should be -- graft --.

Column 4,  
Line 41, "C2-4" should be -- $C_{2-4}$ --.

Column 7,  
Line 1, "-raft" should be -- graft --.

Column 12,  
Line 6, "alkylene" should be -- alkane --.

Signed and Sealed this

Eighth Day of January, 2002

*Attest:*

JAMES E. ROGAN  
*Attesting Officer*   *Director of the United States Patent and Trademark Office*